United States Patent [19]

Weller, III et al.

[11] 4,456,595

[45] Jun. 26, 1984

[54] CARBOXY AND SUBSTITUTED CARBOXY AROLY PEPTIDES

[75] Inventors: Harold N. Weller, III; Eric M. Gordon, both of Pennington, N.J.

[73] Assignee: E. R. Squibb & Sons, Inc., Princeton, N.J.

[21] Appl. No.: 446,923

[22] Filed: Dec. 6, 1982

[51] Int. Cl.³ .................... A61K 37/00; C07C 103/52
[52] U.S. Cl. ............................ 424/177; 260/112.5 R
[58] Field of Search .................. 260/112.5 R; 424/177

[56] References Cited

U.S. PATENT DOCUMENTS

| | | | |
|---|---|---|---|
| 4,052,511 | 10/1977 | Cushman et al. | 424/274 |
| 4,105,776 | 8/1978 | Ondetti et al. | 424/274 |
| 4,105,789 | 8/1978 | Ondetti et al. | 424/309 |
| 4,154,935 | 5/1979 | Ondetti et al. | 546/189 |
| 4,217,359 | 8/1980 | Krapcho | 424/274 |
| 4,248,883 | 2/1981 | Sawayama et al. | 424/274 |
| 4,256,751 | 3/1981 | Hayashi et al. | 424/258 |
| 4,256,761 | 3/1981 | Suh et al. | 424/282 |
| 4,296,033 | 10/1981 | Petrillo et al. | 260/326.2 |
| 4,296,113 | 10/1981 | Ondetti | 424/246 |
| 4,310,461 | 1/1982 | Krapcho et al. | 260/326.2 |
| 4,311,697 | 1/1982 | Krapcho | 424/240 |
| 4,316,905 | 2/1982 | Krapcho | 424/274 |
| 4,316,906 | 2/1982 | Ondetti et al. | 424/274 |
| 4,337,201 | 6/1982 | Petrillo | 548/413 |

FOREIGN PATENT DOCUMENTS

| | | |
|---|---|---|
| 12401 | 6/1980 | European Pat. Off. . |
| 52991 | 11/1981 | European Pat. Off. . |
| 1527 | 3/1981 | South Africa . |
| 2048863 | 12/1980 | United Kingdom . |

*Primary Examiner*—Delbert R. Phillips
*Attorney, Agent, or Firm*—Lawrence S. Levinson; Stephen B. Davis

[57] ABSTRACT

Peptides of the formula

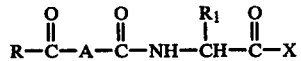

wherein X is various amino or imino acids or esters are useful as hypotensive agents.

18 Claims, No Drawings

CARBOXY AND SUBSTITUTED CARBOXY AROLY PEPTIDES

BACKGROUND OF THE INVENTION

Various carboxyalkyl peptides possessing angiotensin converting enzyme inhibition activity are disclosed by Patchett et al. in European Patent Application Ser. No. 12,401 and by Petrillo et al. in European Patent Application Ser. No. 52991.

Various carboxy alkanoyl amino and imino acids possessing angiotensin converting enzyme inhibition activity are disclosed by Cushman et al. in U.S. Pat. No. 4,052,511 and Ondetti et al. in U.S. Pat. No. 4,105,789.

Mercaptoacyl and acylmercaptoacyl derivatives of proline and substituted prolines are known to be useful hypotensive agents due to their angiotensin converting enzyme inhibition activity. Ondetti, et al. in U.S. Pat. No. 4,105,776 disclose such compounds wherein the proline ring is unsubstituted or substituted by an alkyl or hydroxy group. Ondetti et al. in U.S. Pat. No. 4,154,935 disclose such compounds wherein the proline ring is substituted with one or more halogens. Ondetti, et al. in U.S. Pat. No. 4,316,906 disclose such compounds wherein the proline ring is substituted by various ethers and thioethers. Krapcho in U.S. Pat. No. 4,217,359 disclose such compounds wherein the proline ring has a carbamoyloxy substituent. Krapcho in U.S. Pat. No. 4,311,697 discloses compounds wherein the proline ring has a diether, dithioether, ketal or thioketal substituent in the 4-position. Krapcho in U.S. Pat. No. 4,316,905 discloses such compounds wherein the proline ring has a cycloalkyl, phenyl, or phenyl-lower alkylene substituent. Ondetti in U.S. Pat. No. 4,296,113 discloses such compounds wherein the proline has a keto substituent in the 4-position. Krapcho et al. in U.S. Pat. No. 4,310,461 disclose such compounds wherein the proline has an imido, amido, or amino substituent in the 4-position. Petrillo et al. in U.S. Pat. No. 4,296,033 disclose such compounds wherein the proline has an azido substituent in the 4-position. Suh et al. in U.S. Pat. No. 4,256,761 disclose that mercaptoacyl and acylmercaptoacyl derivatives of various N-substituted amino acids also possess angiotensin converting enzyme inhibition activity.

Mercaptoacyl derivatives of dihydroisoindole carboxylic acids and tetrahydroisoquinoline carboxylic acids are disclosed as being useful hypotensive agents by Ondetti et al. in U.S. Ser. No. 69,031, filed Aug. 23, 1979. These mercaptoacyl tetrahydroisoquinoline compounds are also disclosed by Portlock in U.K. Application No. 2,048,863 and by Hayashi et al. in U.S. Pat. No. 4,256,751.

Mercaptoacyl and acylmercaptoacyl derivatives of various dipeptides are disclosed as possessing angiotensin converting enzyme inhibition activity by Sawayama et al. in U.S. Pat. No. 4,248,883 and by Ondetti et al. in South African Pat. No. 80/1527.

Petrillo in U.S. Pat. No. 4,337,201 discloses that various esters of phosphinylalkanoyl proline and substituted proline possess angiotensin converting enzyme inhibition activity.

SUMMARY OF THE INVENTION

The novel carboxy and substituted carboxy aroyl peptides of this invention are of the formula

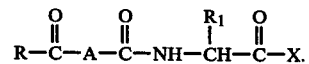

A is

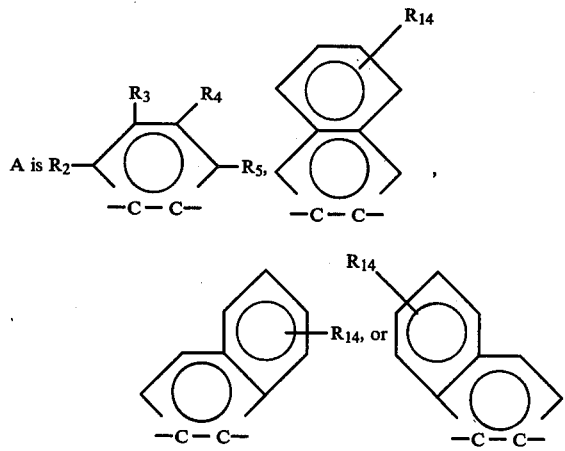

R is hyroxy, lower alkoxy, lower alkyl,

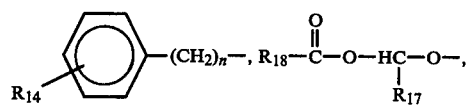

lower alkoxy—NH—, or —OM wherein M is an alkali metal salt ion such as sodium, potassium, or lithium or an alkaline earth metal salt ion such as calcium or magnesium.

$R_1$ is hydrogen, lower alkyl, halo substituted lower alkyl,

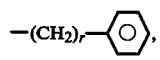

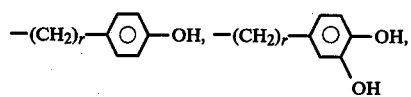

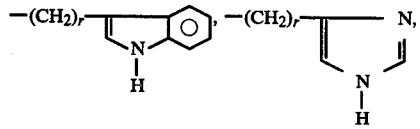

—$(CH_2)_r$—$NH_2$—$(CH_2)_r$—SH, —$(CH_2)_r$—OH, —$(CH_2)_r$—S-lower alkyl,

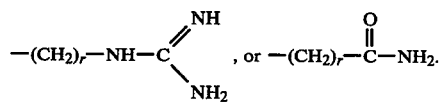

$R_2$, $R_3$, $R_4$ and $R_5$ are independently selected from hydrogen, lower alkyl of 1 to 4 carbons, lower alkoxy of 1 to 4 carbons, lower alkylthio of 1 to 4 carbons,

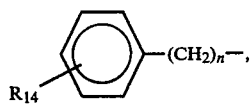

hydroxy, nitro, halo, halo substituted lower alkyl of 1 to 4 carbons, hydroxy substituted lower alkyl of 1 to 4 carbons, lower

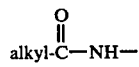

wherein said lower alkyl is of 1 to 4 carbons, or

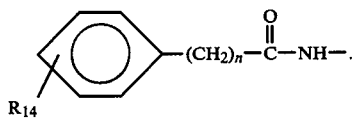

X is an amino or imino acid of the formula

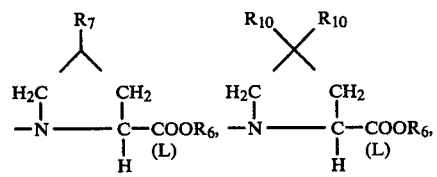

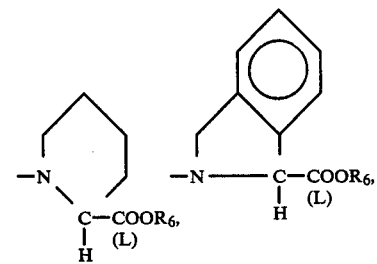

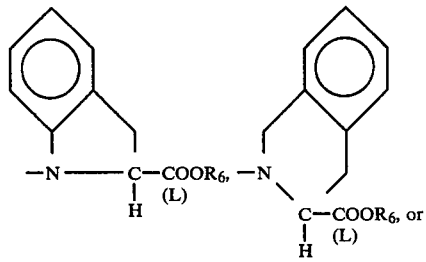

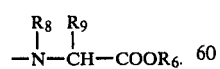

$R_7$ is hydrogen, lower alkyl, halogen, keto, hydroxy,

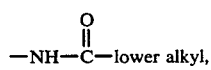

azido, amino,

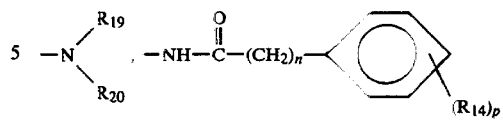

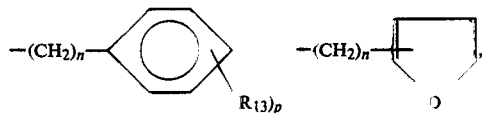

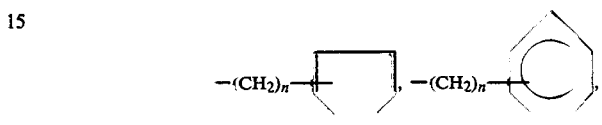

a 1- or 2-naphthyl of the formula

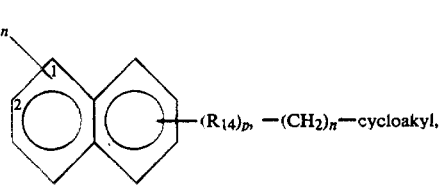

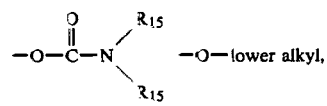

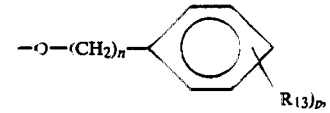

a 1- or 2-naphthyloxy of the formula

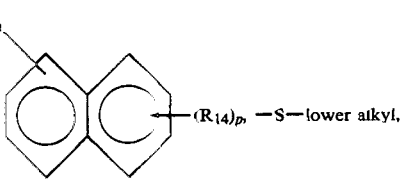

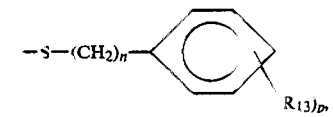

or a 1- or 2-naphthylthio of the formula

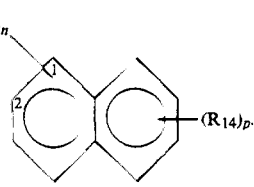

$R_{10}$ is halogen or $-Y-R_{16}$.

$R_{13}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

$R_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy.

n is zero, one, two, three, or four.

p is one, two or three provided that p is more than one only if $R_{13}$ or $R_{14}$ is hydrogen, methyl, methoxy, chloro, or fluoro.

$R_{15}$ is hydrogen or lower alkyl of 1 to 4 carbons.

Y is oxygen or sulfur.

$R_{16}$ is lower alkyl of 1 to 4 carbons,

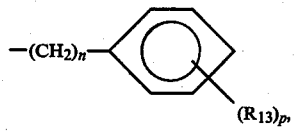

or the $R_{16}$ groups join to complete an unsubstituted 5- or 6-membered ring or said ring in which one or more of the carbons has a lower alkyl of 1 to 4 carbons or a di(lower alkyl of 1 to 4 carbons) substituent.

$R_8$ is hydrogen, lower alkyl, cycloalkyl of 3 to 7 carbons, or

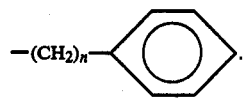

$R_9$ is hydrogen, lower alkyl,

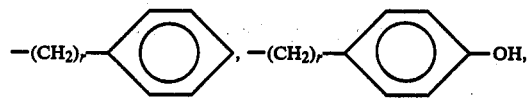

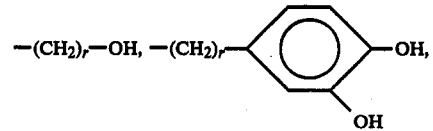

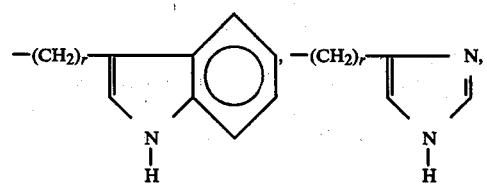

$-(CH_2)_r-NH_2, (CH_2)_r-SH, -(CH_2)_r-S-$lower alkyl,

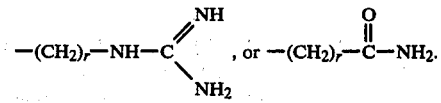

r is an integer from 1 to 4.

$R_{19}$ is lower alkyl, benzyl, or phenethyl.

$R_{20}$ is hydrogen, lower alkyl, benzyl or phenethyl.

$R_6$ is hydrogen, lower alkyl, benzyl, benzhydryl, a salt forming ion such as an alkali metal salt ion such as sodium, potassium, or lithium or an alkaline earth metal salt ion such as calcium or magnesium, or

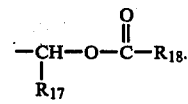

$R_{17}$ is hydrogen, lower alkyl, cycloalkyl of 3 to 7 carbon atoms, or phenyl.

$R_{18}$ is hydrogen, lower alkyl, lower alkoxy, or phenyl.

DETAILED DESCRIPTION OF THE INVENTION

This invention in its broadest aspects relates to the carboxy and substituted carboxy aroyl peptide compounds of formula I above, to compositions containing such compounds, and to the method of using such compounds as pharmaceutical agents.

The term lower alkyl used in defining various symbols refers to straight or branched chain radicals having up to seven carbons. The preferred lower alkyl groups are up to four carbons with methyl and ethyl most preferred. Similarly the terms lower alkoxy and lower alkylthio refer to such lower alkyl groups attached to an oxygen or sulfur.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc. Similarly, the term hydroxy substituted lower alkyl refers to such lower alkyl groups in which one or more hydrogens have been replaced by hydroxy groups such as hydroxymethyl, 2-hydroxyethyl, etc.

The symbols

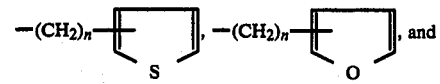

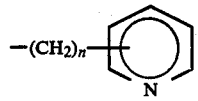

represent that the alkylene bridge is attached to an available carbon atom.

The compounds of formula I may be obtained by coupling a carboxylic acid of the formula

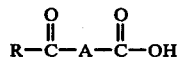 (II)

with the peptide ester of the formula

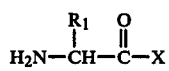 (III)

wherein $R_6$ in the definition of X is an easily removable ester protecting group such as benzhydryl, benzyl or t-butyl. This coupling reaction can be accomplished using any one of the numerous techniques well known in the art. For example, the reaction can be performed in the presence of a coupling agent such as a carbodiimide, preferably dicyclohexylcarbodiimide. Alternatively, the carboxylic acid of formula II can be activated by formation of its mixed anhydride, symmetrical anhydride, acid chloride or active ester or by use of Woodward reagent K or N-ethoxycarbonyl-2-ethoxy 1,2-dihydroquinoline. Following completion of the coupling, the $R_6$ protecting group is removed for example by hydrogenation when $R_6$ is benzyl or treatment with trifluoroacetic acid when $R_6$ is t-butyl to yield the products of formula I wherein $R_6$ is hydrogen.

In the above reaction if any or all of R, $R_1$, $R_2$, $R_3$, $R_4$, $R_5$, $R_8$, or $R_9$ are hydroxy, amino,

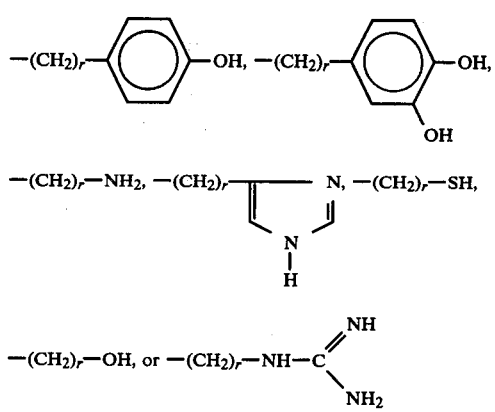

then the hydroxyl, amino, imidazolyl, mercaptan or guanidinyl function should be protected during the reaction. Suitable protecting groups include benzyloxycarbonyl, t-butoxycarbonyl, t-butyl, benzyl, benzhydryl, trityl, etc., and nitro in the case of guanidinyl. The protecting group is removed by hydrogenation, treatment with acid, or other known methods following completion of the reaction.

The ester products of formula I wherein $R_6$ is lower alkyl, benzyl or benzhydryl can be chemically treated such as with sodium hydroxide in aqueous dioxane to yield the products of formula I wherein $R_6$ is hydrogen. The benzyl and benzhydryl esters can also be hydrogenated, for example, by treating with hydrogen in the presence of a palladium on carbon catalyst.

The ester products of formula I wherein $R_6$ is

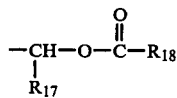

may be obtained by employing the peptide of formula III in the above reactions with such ester group already in place. Such ester reactants can be prepared by treating the peptide of formula III wherein $R_6$ is hydrogen with a reagent such as

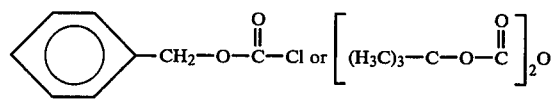

so as to protect the N-atom. The protected peptide is then reacted in the presence of a base with a compound of the formula

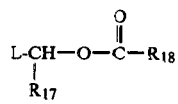

(IV)

wherein L is a leaving group such as chlorine, bromine, tolylsulfonyloxy, etc., followed by removal of the N-protecting group such as by treatment with acid or hydrogenation.

The ester products of formula I wherein $R_6$ is

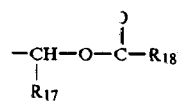

can also be obtained by treating the product of formula I wherein $R_6$ is hydrogen with a molar excess of the compound of formula IV. The diester products wherein

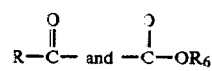

are the same and are

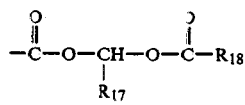

can be obtained by treating the product of formula I wherein

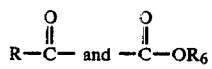

are both

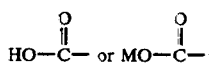

with two or more equivalents of the compound of formula IV.

The ester products of formula I wherein R is

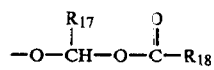

can be obtained by employing the carboxylic acid of formula II in the coupling reaction with the R ester group already in place. Alternatively, these ester products can be obtained by treating the product of formula I wherein R is hydroxy or —OM and $R_6$ is benzyl or benzhydryl with the compound of formula IV in the presence of base. Removal of the $R_6$ ester group such as by hydrogenation yields the products of formula I wherein R is

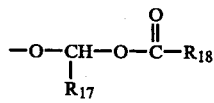

and R₆ is hydrogen.

The peptide ester of formula III may be obtained by coupling the hydrochloride salt of the amino or imino acid ester of the formula (V) HX wherein R₆ is, for example, benzyl with the N-protected amino acid of the formula

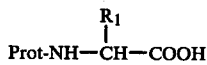

wherein Prot is a protecting group such as

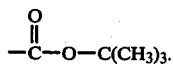

Preferably, this reaction is performed in the presence of a coupling agent such as dicyclohexylcarbodiimide. Removal of the N-protecting group, for example, by treatment with trifluoroacetic acid yields the peptide ester of formula III.

The carboxylic acids of formula II are prepared by conventional procedures.

Preferred compounds of this invention with respect to the peptide part of the structure of formula I are those wherein:

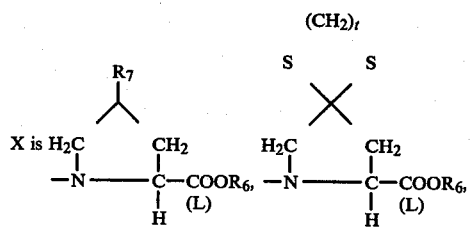

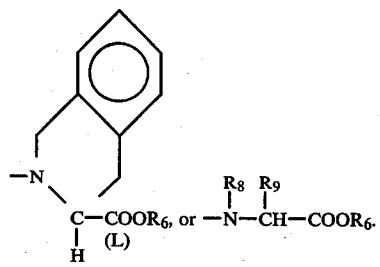

R₁ and R₉ are independently selected from hydrogen, straight or branched chain lower alkyl of 1 to 4 carbons,

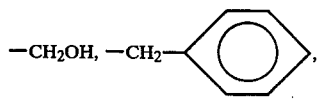

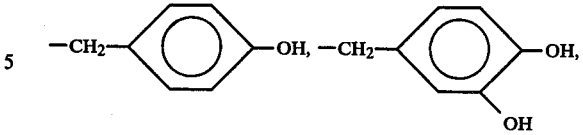

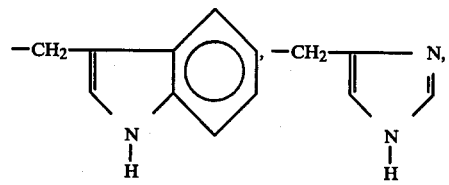

−(CH₂)₄−NH₂, −CH₂−SH, −(CH₂)₂−S−CH₃,

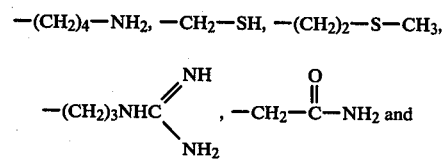

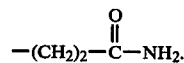

R₇ is hydrogen, cyclohexyl, lower alkoxy of 1 to 4 carbons,

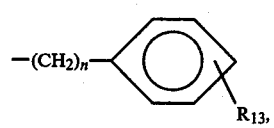

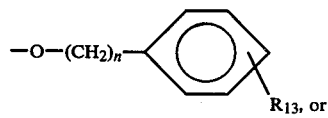

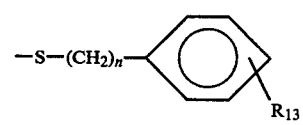

wherein n is zero, one, or two and R₁₃ is hydrogen, methyl, methoxy, methylthio, Cl, Br, F, or hydroxy.

t is two or three.

R₆ is hydrogen, an alkali metal salt, straight or branched chain alkyl of 1 to 4 carbons, or

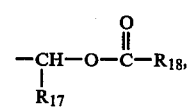

R₁₇ is hydrogen, straight or branched chain lower alkyl of 1 to 4 carbons, or cyclohexyl and R₁₈ is straight or branched chain lower alkyl of 1 to 4 carbons or phenyl.

R₈ is hydrogen or cycloalkyl of 5 to 7 carbons.

Most preferred compounds of this invention with respect to the peptide part of the structure of formula I are those having the peptide

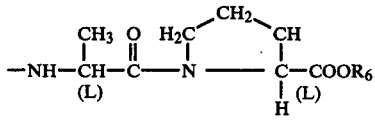

wherein R₆ is hydrogen, ethyl,

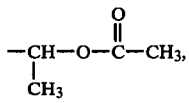

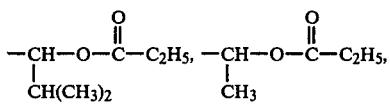

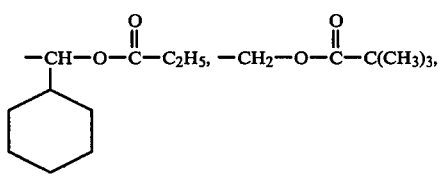

or an alkali metal salt.

Preferred compounds of this invention with respect to the carboxyaroyl portion of the structure of formula I are those wherein:

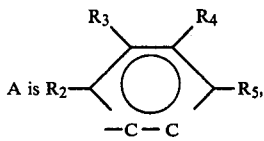

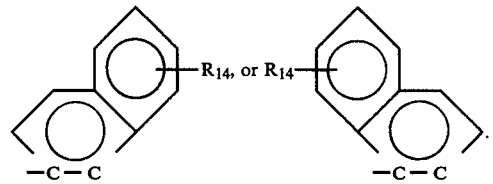

R₂, R₃, R₄ and R₅ are independently selected from hydrogen, methyl, methoxy, methylthio, hydroxy, phenyl, benzyl, nitro, halo, trifluoromethyl,

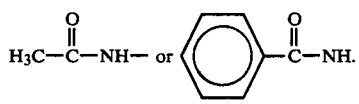

R₁₄ is hydrogen, methyl, methoxy, methylthio, Cl, Br, F or hydroxy.

R is hydroxy, ethoxy, —OM,

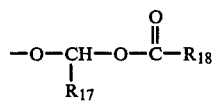

wherein R₁₇ is hydrogen, straight or branched chain lower alkyl of 1 to 4 carbons, or cyclohexyl and R₁₈ is straight or branched chain lower alkyl of 1 to 4 carbons or phenyl, especially wherein R is hydroxy or —OM.

The compounds of formula I wherein R₆ is hydrogen and/or R is hydroxy form salts with a variety of inorganic or organic bases. The nontoxic, pharmaceutically acceptable salts are preferred, although other salts are also useful in isolating or purifying the product. Such pharmaceutically acceptable salts include alkali metal salts such as sodium, potassium or lithium, alkaline earth metal salts such as calcium or magnesium, and salts derived from amino acids such as arginine, lysine, etc. The salts are obtained by reacting the acid form of the compound with an equivalent of the base supplying the desired ion in a medium in which the salt precipitates or in aqueous medium and then lyophilizing.

The peptide portion of the molecule of the products of formula I represented by

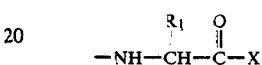

is in the L-configuration.

The products of formula I wherein the imino acid ring is monosubstituted also give rise to cis-trans isomerism. The configuration of the final product will depend upon the configuration of the R₇ substituent in the starting material of formula V.

The compounds of formula I, and the pharmaceutically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood, produces angiotensin I. Angiotensin I is converted by angiotensin converting enzyme (ACE) to angiotensin II. The latter is and active pressor substance which has been implicated as the causative agent in several forms of hypertension in various mammalian species, e.g., humans. The compounds of this invention intervene in the angiotensinogen→(renin)→angiotensin I→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of formula I wherein X is

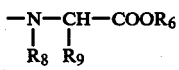

also possess enkephalinase inhibition activity and are useful as analgesic agents. Thus, by the administration of a composition containing one or a combination of such compounds of formula I or a pharmaceutically acceptable salt thereof, pain is alleviated in the mammalian host. A single dose, or preferably two to four divided daily doses, provided on a basis of about 0.1 to about 100 mg. per kilogram of body weight per day, preferably about 1 to about 50 mg. per kilogram per day, produces the desired analgesic activity. The composition is preferably administered orally but parenteral routes such as subcutaneous can also be employed.

The following examples are illustrative of the invention. Temperatures are given in degrees centigrade.

EXAMPLE 1

1-[N-[(2-Carboxyphenyl)carbonyl]-L-alanyl]-L-proline (a) 1-[N-[(2-Carboxyphenyl)carbonyl]-L-alanyl]-L-proline, phenylmethyl ester L-Alanyl-L-proline, phenylmethyl ester, p-toluenesulfonic acid salt (4.65 g., 11.1 mmole) is dissolved in 10% aqueous sodium bicarbonate (250 ml.) and extracted with methylene chloride (4×125 ml.). The combined extracts are dried (MgSO$_4$) and concentrated to a volume of approximately 100 ml., to which is added phthalic anhydride (1.6 g., 11 mmole). The resulting solution is stirred at room temperature for 66 hours, then poured into a saturated solution of aqueous sodium bicarbonate (200 ml.) and shaken. The methylene chloride layer is discarded. The aqueous layer is acidified with 1N hydrochloric acid, extracted with methylene chloride (4×150 ml.) and dried (MgSO$_4$). Removal of the solvent leaves a white foamy solid which is dissolved in chloroform, filtered, and reconcentrated to give 3.2 g. of 1-[N-[(2-carboxyphenyl)carbonyl]-L-alanyl]-L-proline, phenylmethyl ester.

(b) 1-[N-[(2-Carboxyphenyl)carbonyl]-L-alanyl]-L-proline

To a stirring suspension of 5% palladium on carbon catalyst (0.45 g.) in methanol (10 ml.) is added a solution of the ester product from part (a) (3.2 g., 7.5 mmole) in methanol (40 ml.). The resulting solution is purged with argon for 15 minutes, then stirred under a constant stream of hydrogen for 4.5 hours. The reaction mixture is then purged again with argon, filtered, and concentrated. The residue is dissolved in water (75 ml.) and lyophilized to give 2.5 g. of 1-[N-[(2-carboxyphenyl)carbonyl]-L-alanyl]-L-proline as a white powder; m.p. (105) 118°. TLC (silica gel R$_f$=0.5, n-butanol:acetic acid, 3:1). $[\alpha]_D^{25}$=−125° (c=0.5, ethanol)

Anal. calc'd. for C$_{16}$H$_{18}$N$_2$O$_6$.0.5H$_2$O: C, 55.84; H, 5.56; N, 8.14; Found: C, 55.84; H, 5.48; N, 8.14.

EXAMPLE 2

1-[N-(2-Carboxy-4,5-dichlorobenzoyl)-L-alanyl]-L-proline (a) 4,5-Dichlorophthalic anhydride 4,5-Dichlorophthalic acid (30 g., 0.127 mole) is refluxed in 150 ml. of acetic anhydride for 3 hours. The acetic anhydride is evaporated and the residue is triturated with diethyl ether and filtered to give a quantitative yield of 4,5-dichlorophthalic anhydride. The crude product is recrystallized from ethyl acetate and hexane.

(b) 4,5-Dichlorophthalic acid, mono(phenylmethyl)ester

To a mixture of 4,5-dichlorophthalic anhydride (9.5 g., 43.8 mmole) and benzyl alcohol (4.73 g., 43.8 mmole) in methylene chloride is added a dropwise solution of triethylamine in methylene chloride while maintaining a temperature of 20°–25°. The reaction mixture is stirred at room temperature for 24 hours. The solvent is evaporated and the mixture is dissolved in ethyl acetate and extracted into sodium bicarbonate solution. The aqueous phase is washed with ethyl acetate then acidified with 15% potassium bisulfate and the product is extracted into fresh ethyl acetate. The ethyl acetate solution is washed with water and brine and dried (MgSO$_4$). The solvent is evaporated to leave 11.65 g. of 4,5-dichlorophthalic acid, mono(phenylmethyl)ester as a white solid.

(c) 1-[N-(2-Carboxy-4,5-dichlorobenzoyl-L-alanyl]-L-proline, bis(phenylmethyl)ester 4,5-Dichlorophthalic acid, mono(phenylmethyl)ester (1 g.) is dissolved in 30 ml. of methylene chloride and 2 ml. of oxalyl chloride are added. The solution is cooled to 0°–5° and a catalytic amount of dimethylformamide is added. The reaction solution is stirred at room temperature for 3 hours. The solution is concentrated to a residue. To this residue is added L-alanyl-L-proline, phenylmethyl ester, p-toluenesulfonic acid salt (1.38 g., 1 eq.), tetrahydrofuran (30 ml.) and triethylamine (0.62 g., 2 eq.). The reaction mixture is stirred at room temperature for 20 hours. The solvent is evaporated and the residue is dissolved in ethyl acetate. The ethyl acetate solution is washed with water, 1N sodium bicarbonate, 5% hydrochloric acid, sodium bicarbonate and brine. After drying (MgSO$_4$), the solution is concentrated to an oily residue. Purification by flash chromatography on silica gel (methylene chloride:ethyl acetate, 10:1) gives 1.65 g. of 1-[N-(2-carboxy-4,5-dichlorobenzoyl)-L-alanyl]-L-proline, bis(phenylmethyl)ester.

(d) 1-[N-(2-Carboxy-4,5-dichlorobenzoyl)-L-alanyl]-L-proline

The diester product from part (c) (1.34 g.) is saponified by stirring in 10% sodium hydroxide (5 ml.) and methanol (5 ml.) for one hour. The reaction solution is diluted with water and washed with diethyl ether. The aqueous phase is acidified and sodium chloride is added to saturate. The product is extracted into ethyl acetate. The ethyl acetate layer is washed with brine and dried (MgSO$_4$). Evaporation of the solvent gives the crude diacid which is purified by slurrying in diethyl ether and decanting several times to give 0.7 g. of 1-[N-(2-carboxy-4,5-dichlorobenzoyl)-L-alanyl]-L-proline; m.p. 134°-137°. TLC (silica gel $R_f$=0.35, ethyl acetate:-pyridine:acetic acid:water; 45:20:6:11). $[\alpha]_D$=−76.5 (c=1.0, methanol).

Anal. calc'd. for $C_{16}H_{16}N_2O_6Cl_2$: C, 47.66; H, 4.00; N, 6.95; Cl, 17.58; Found: C, 47.55; H, 3.99; N, 6.85; Cl, 17.36.

EXAMPLE 3

1-[N-(2-Carboxy-6-nitrobenzoyl)-L-alanyl]-L-proline (a) 3-Nitrophthalic anhydride A sample of commercially obtained 3-nitrophthalic anhydride (partially hydrolyzed to the diacid) is heated at 70° in acetic anhydride for 3 hours. After evaporation of acetic anhydride and washing with ethyl ether, the 3-nitrophthalic anhydride is obtained as pure material.

(b) 1-[N-(2-Carboxy-6-nitrobenzoyl)-L-alanyl]-L-proline, phenylmethyl ester

To a mixture of 3-nitrophthalic anhydride (0.9 g., 4.3 mmole) and L-alanyl-L-proline, phenylmethyl ester, p-toluenesulfonic acid salt (1.93 g., 4.3 mmole) in tetrahydrofuran (30 ml.) is added triethylamine (0.43 g., 4.3 mmole). The reaction mixture is stirred at room temperature for 20 hours. The reaction mixture is then concentrated and the mixture is dissolved in ethyl acetate. After washing the ethyl acetate layer with water, the product is extracted into 1N sodium bicarbonate. The aqueous layer is washed with ethyl acetate and then acidified with potassium bisulfate. The product is extracted into fresh ethyl acetate. The organic phase is washed with water and brine and dreid (MgSO$_4$). Evaporation of the solvent gives 1.9 g. of 1-[N-(2-carboxy-6-nitrobenzoyl)-L-alanyl]-L-proline, phenylmethyl ester as a solid residue. 1 g. of this material is purified on an LH20 column eluting with methanol.

(c) 1-[N-(2-Carboxy-6-nitrobenzoyl)-L-alanyl]-L-proline

The ester product from part (b) (1 g., 2.1 mmole) is stirred in a 10% sodium hydroxide and methanol solution at room temperature for 2.5 hours. The reaction solution is diluted with water and washed with ethyl ether. Upon acidification of the aqueous phase with 10% hydrochloric acid and saturation with sodium chloride, the diacid is extracted via multiple extractions into ethyl acetate. After drying (MgSO$_4$) and evaporating, 0.5 g. of product is obtained as a white solid. In order to remove entrapped solvent, 300 mg. of material is dissolved in water and lyophilized to give pure 1-[N-(2-carboxy-6-nitrobenzoyl)-L-alanyl]-L-proline as a white solid; m.p. 134°-137°. TLC (silica gel $R_f$=0.28, ethyl acetate:pyridine:acetic acid:water; 45:20:6:11). $[\alpha]_D$=−57.2 (c=1.0, methanol).

Anal. calc'd. for $C_{16}H_{17}N_3O_8.0.5H_2O$ C, 49.50; H, 4.67; N, 10.82; Found: C, 49.51; H, 4.63; N, 10.80.

EXAMPLE 4

1-[N-[3-(Acetylamino)-2-carboxybenzoyl]-L-alanyl]-L-proline (a) 3-Aminophthalic acid A commercial sample of 3-nitrophthalic acid (20% 4-nitro by TLC) is dissolved in 150 ml. of hot water, filtered and cooled for 2 hours to give 13 g. of pure 3-nitrophthalic acid as a white solid. The recrystallized 3-nitrophthalic acid (13 g., 0.062 mole) is dissolved in methanol (200 ml.) and hydrogenated over platinic oxide (50 mg.) at 25 psi. When uptake ceases (one hour), the mixture is filtered and evaporated to 12.4 g. of solid 3-aminophthalic acid.

(b) 3-Acetamidophthalic anhydride

3-Aminophthalic acid (4 g., 0.022 mole) is refluxed with 50 ml. of acetic anhydride for 2 hours, then evaporated to a solid. Trituration with ethyl acetate gives 2.5 g. of 3-acetamidophthalic anhydride; m.p. 180°-183°.

(c) 1-[N-[3-(Acetylamino)-2-carboxybenzoyl]-L-alanyl]-L-proline, phenylmethyl ester 3-Acetamidophthalic anhydride (2.5 g., 0.012 mole) and L-alanyl-L-proline, phenylmethyl ester, p-toluenesulfonic acid salt (5.46 g., 0.012 mole) is slurried in 100 ml. of methylene chloride, cooled to 0°, and treated with triethylamine (2.5 g., 0.025 mole). The mixture is allowed to come to room temperature overnight and is afterward evaporated to an oil. This oil is taken up in ethyl acetate and washed with dilute hydrochloric acid, water, and saturated sodium chloride. Drying (Na$_2$SO$_4$) and evaporation gives an oil containing two components. After standing in a small volume of ethyl acetate, 2.1 g., of 1-[N-[3-(acetylamino)-2-carboxybenzoyl]-L-alanyl]-L-proline, phenylmethyl ester are obtained; m.p. 158°-160°.

(c) 1-[N-[3-(Acetylamino)-2-carboxybenzoyl]-L-alanyl]-L-proline

A solution of the ester product from part (b) (2.1 g., 4.2 mmole) in methanol (150 ml.) is hydrogenated over 10% palladium on carbon catalyst (0.2 g.) overnight at 25 psi. The catalyst is filtered off and the solution is evaporated in vacuo to an oil. Trituration with isopropyl ether gives an impure solid; m.p. 97°-99°. Purification on a 200 g. LH 20 column in methanol gives a pure fraction which is evaporated and triturated with isopropyl ether to give 0.4 g. of solid diacid product; m.p. 127°-130°. This material is dissolved in water, filtered (millipore) and lyophilized to a fluffy white powder. Drying (P$_2$O$_5$) in vacuo gives an analytical sample of 1-[N-[3-(acetylamino)-2-carboxybenzoyl]-L-alanyl]-L-proline; m.p. 127°-128°. TLC (silica gel $R_f$=0.48, ethyl acetate:pyridine:acetic acid:water; 60:20:6:11). $[\alpha]_D$=−121.3° (c=1.0, methanol).

Anal. Calc'd. for $C_{18}H_{21}N_3O_7.0.67H_2O$: C, 53.59; H, 5.58; N, 10.42; Found: C, 53.66; H, 5.52; N, 10.53.

EXAMPLE 5

1-[N-[[2-Carboxy-1-naphthalenyl]carbonyl]-L-alanyl]-L-proline, dilithium salt and 1-[N-[[1-carboxy-2-napthalenyl]carbonyl]-L-alanyl]-L-proline, dilithium salt (a) 1,2-Naphthalenedicarboxylic acid, 1-mono(phenylmethyl)ester and 1,2-naphthalenedicarboxylic, 2-mono(phenylmethyl)ester A solution of 1,2-naphthalic anhydride (3.0 g., 15.3 mmole) [prepared as described in Organic Synthesis, Coll. Vol. II, p. 432] and diisopropylethylamine (1 ml.) in benzyl alcohol is stirred at room temperature for 22 hours. The resulting solution is poured into 10% sodium bicarbonate solution and washed with ethyl acetate. The aqueous layer is then acidified and extracted with ethyl acetate and ether. The combined organic extracts are dried (MgSO$_4$) and concentrated to give 2.3 g. of the mixture of 1,2-naphthalene dicarboxylic acid, 1-mono(phenylmethyl)ester and 1,2-naphthalenedicarboxylic acid, 2-mono(phenylmethyl)ester; TLC (silica gel $R_f$=0.18, 0.22, 3% methanol in methylene chloride).

(b) 1-[N-[[2-Carboxy-1-naphthalenyl]carbonyl]-L-alanyl]-L-proline, bis(phenylmethyl)ester and 1-[N-

[[1-carboxy-2-naphthalenyl]carbonyl]-L-alanyl]-L-proline, bis(phenylmethyl)ester To a stirring solution of the ester mixture from part (a) (2.3 g., 8.4 mmole) in tetrahydrofuran are added L-alanyl-L-proline, phenylmethyl ester, p-toluenesulfonic acid salt (3.8 g., 8.4 mmole), dicyclohexylcarbodiimide (1.7 g., 8.4 mmole), dicyclohexylcarbodiimide (1.7 g., 8.4 mmole), 1-hydroxybenzotriazole hydrate (1.1 g., 8.4 mmole), and diisopropylethylamine (1.5 ml., 8.4 mmole). The resulting solution is stirred at room temperature for 20 hours. The mixture is then filtered, concentrated, dissolved in ethyl acetate, and filtered again. The resulting solution is washed sequentially with 1N hydrochloric acid, 10% sodium bicarbonate and water, dried (MgSO₄), and concentrated. The residue is chromatographed on silica gel LP-1 using methylene chloride:ethyl acetate (8:1) as eluant. Fractions are monitored by TLC (silica gel, methylene chloride:ethyl acetate, 8:1) and those containing the desired product ($R_f$=0.5, isomers not separable) are combined and concentrated to give 1.0 g. of a mixture of 1-[N-[[2-carboxy-1-naphthalenyl]carbonyl]-L-alanyl]-L-proline, bis(phenylmethyl)ester and 1-[N-[[1-carboxy-2-naphthalenyl]-carbonyl]-L-alanyl]-L-proline, bis(phenylmethyl)ester as a clear oil.

(c) 1-[N-[[2-Carboxy-1-naphthalenyl]carbonyl]-L-alanyl]-L-proline, dilithium salt and 1-[N-[[1-carboxy-2-naphthalenyl]carbonyl]-L-alanyl]-L-proline, dilithium salt A solution of the bis(phenylmethyl)ester mixture from part (b) (0.5 g., 0.89 mmole) in ethanol with 10% palladium on carbon catalyst is stirred under a stream of hydrogen for 3 hours. Following completion of the reaction (TLC), the resulting solution is filtered, concentrated, and dissolved in 1N lithium hydroxide (0.8 ml.). This aqueous solution is washed with ether and applied to an AG50W×2 (Li⁺) column eluting with water. The resulting material is concentrated and chromatographed on HP-20 with water as the eluant. Fractions are monitored by TLC and those containing the desired product are combined and lyophilized to give 0.15 g. of the white solid mixture of 1-[N-[[2-carboxy-1-naphthalenyl]-carbonyl]-L-alanyl]-L-proline, dilithium salt and 1-[N-[[1-carboxy-2-naphthalenyl]carbonyl]-L-alanyl]-L-proline, dilithium salt; m.p. 210°. TLC (silica gel $R_f$=0.67 (major), 0.57 (minor), n-butanol:ethyl acetate:acetic acid:water; 1:1:1:1). $[\alpha]_D = -79°$ (c=0.5, water).

Anal. calc'd. for $C_{20}H_{18}N_2O_6Li_2 \cdot 2.4H_2O$: C, 54.82; H, 5.24; N, 6.39; Found: C, 54.82; H, 5.10; N, 6.43.

EXAMPLES 6-51

Following the procedure of Example 1 but substituting for the L-alanyl-L-proline, phenylmethyl ester the imino or amino acid ester shown below in Col. I one obtains the ester product shown in Col. II. Hydrogenation or acid treatment yields the corresponding diacid which can then be converted to the disalt.

Col. I

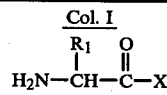

Col. II

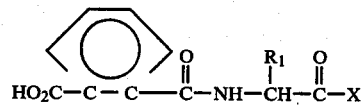

| Example | R₁ | X |
|---------|-----|---|
| 6 | —CH₃ | 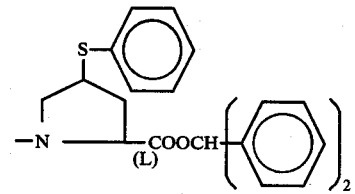 |
| 7 | —CH₃ | 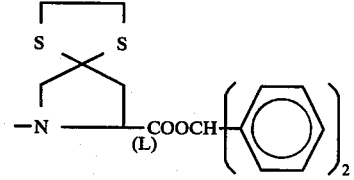 |
| 8 | —CH₃ | 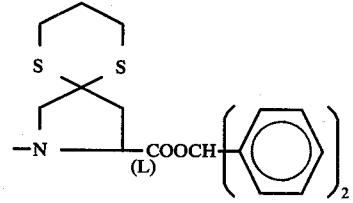 |

-continued
Col. I
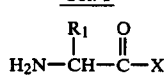
Col. II
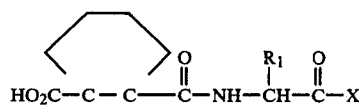
| Example | R₁ | X |
|---|---|---|
| 9 | —C(CH₃)₃ | 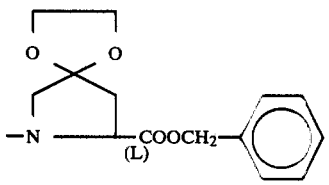 |
| 10 | —CH₃ | 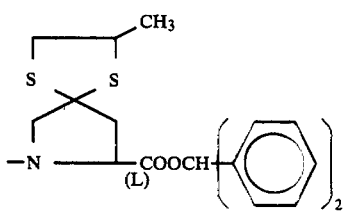 |
| 11 | —CH₃ | 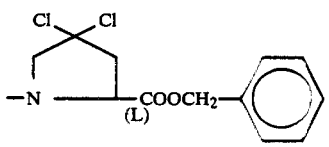 |
| 12 | —CH₃ | 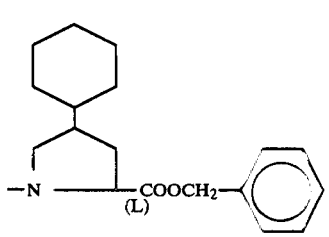 |
| 13 | —CH₃ | 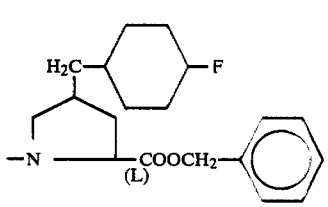 |
| 14 | —CH₃ | 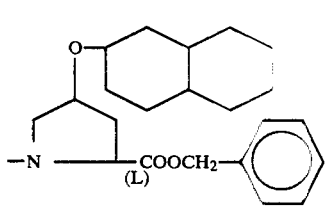 |

-continued
Col. I
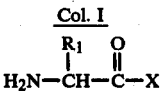
Col. II
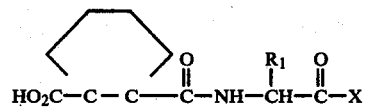
| Example | R₁ | X |
|---|---|---|
| 15 | —CH₃ | 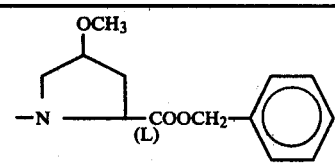 |
| 16 | —CH₃ | 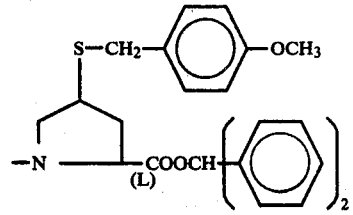 |
| 17 | —CH₃ | 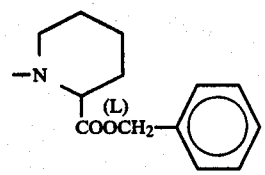 |
| 18 | —CH₃ | 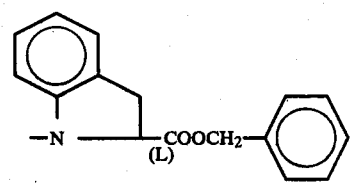 |
| 19 | —CH₃ | 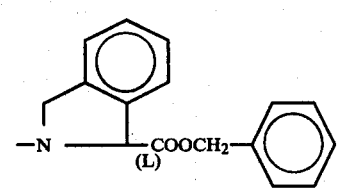 |
| 20 | —CH₃ | 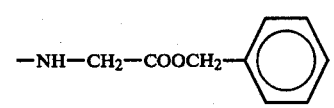 |
| 21 | —CH₃ | 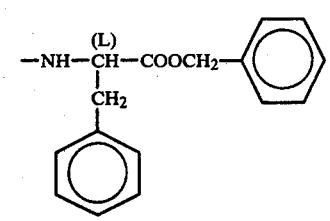 |

-continued
Col. I
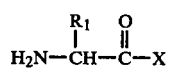
Col. II
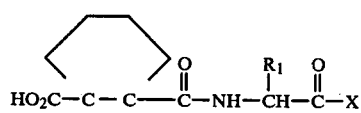
| Example | R₁ | X |
|---|---|---|
| 22 | —CH₃ | 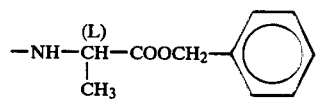 |
| 23 | —CH₃ | 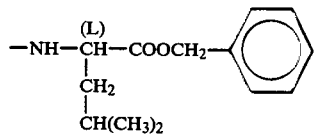 |
| 24 | —CH₃ | 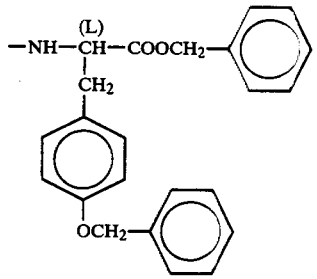 |
| 25 | —CH₃ | 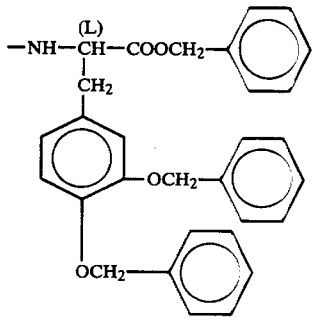 |
| 26 | —CH₃ | 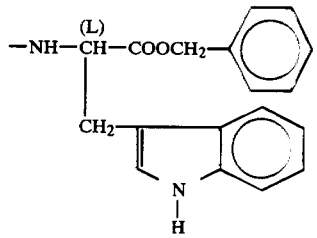 |

-continued
Col. I
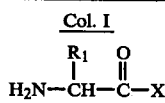
Col. II
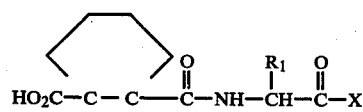
| Example | R₁ | X |
|---------|-----|---|
| 27 | —CH₃ | 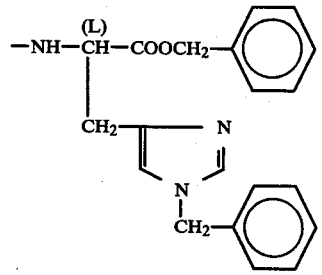 |
| 28 | —CH₃ | 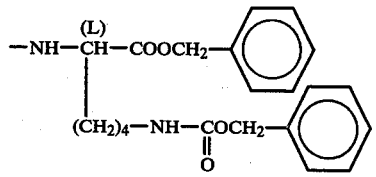 |
| 29 | —CH₃ | 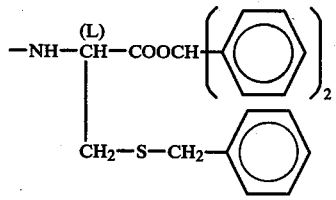 |
| 30 | —CH₃ | 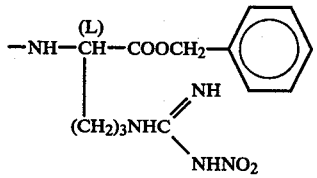 |
| 31 | —CH₃ | 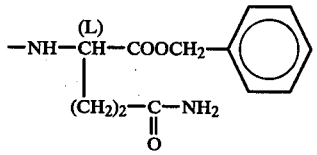 |
| 32 | —CH₃ | 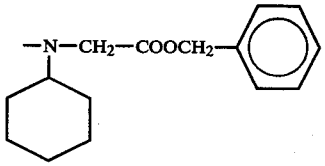 |

-continued
Col. I
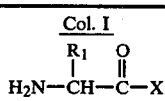
Col. II
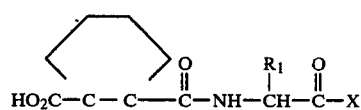
| Example | R₁ | X |
|---|---|---|
| 33 | —CH₃ | 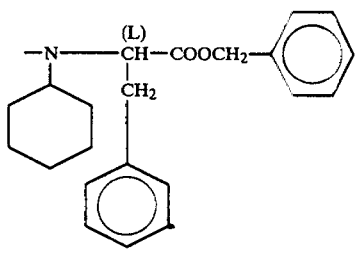 |
| 34 | —CH₃ | 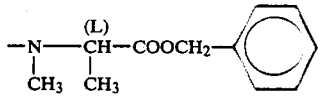 |
| 35 | —CH₃ | 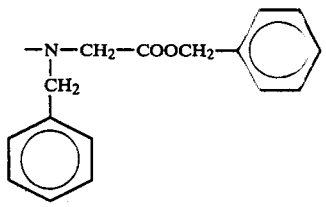 |
| 36 | —H | 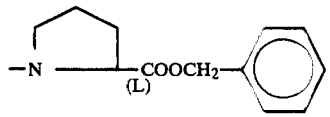 |
| 37 | —C₂H₅ | 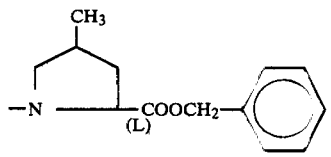 |
| 38 | —CH₃ | 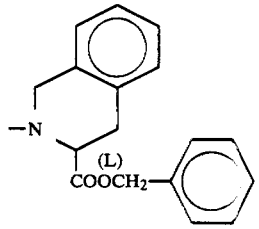 |
| 39 | 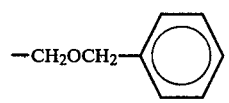 | 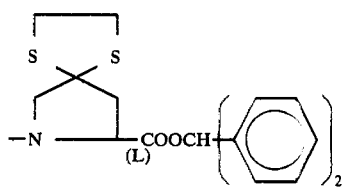 |

-continued
Col. I
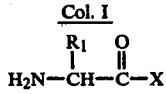
Col. II
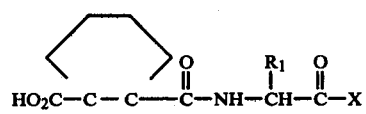
| Example | R₁ | X |
|---|---|---|
| 40 | 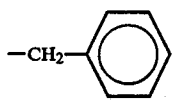 | 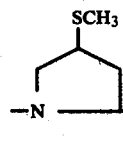 |
| 41 | 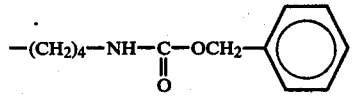 | 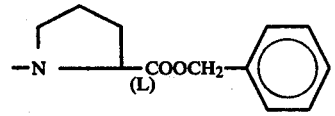 |
| 42 | 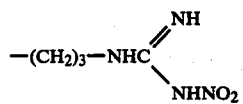 | 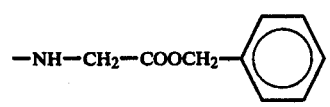 |
| 43 | 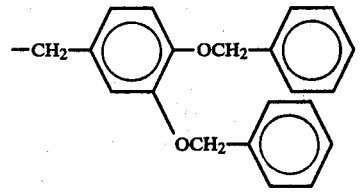 | 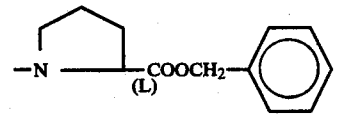 |
| 44 | —CH₃ | 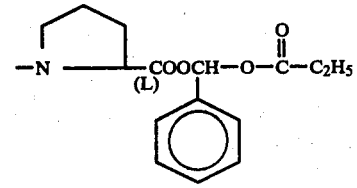 |
| 45 | —CH₃ | 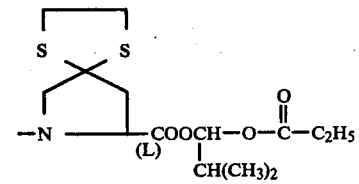 |
| 46 | —CH₃ | 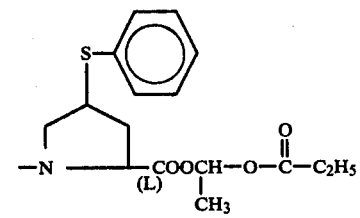 |

-continued

Col. I $$H_2N-\underset{\underset{R_1}{|}}{CH}-\underset{\underset{}{||}}{C}-X$$
$$\phantom{H_2N-CH-}\overset{O}{\phantom{|}}$$

Col. II

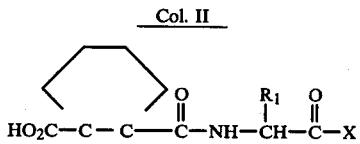

$$HO_2C-C-C-\underset{\underset{}{||}}{C}-NH-\underset{\underset{R_1}{|}}{CH}-\underset{\underset{}{||}}{C}-X$$

| Example | $R_1$ | X |
|---|---|---|
| 47 | —CH₃ | —N⟨pyrrolidine⟩—COOCH₂—O—C(=O)—C(CH₃)₃ (L) |
| 48 | —CH₃ | —N⟨pyrrolidine⟩—COOCH₂—O—C(=O)—C₆H₅ (L) |
| 49 | —CH₃ | —N⟨pyrrolidine⟩—COOC₂H₅ (L) |
| 50 | —CH₃ | —N⟨pyrrolidine⟩—COOCH(CH₃)—O—C(=O)—CH₃ (L) |
| 51 | —CH₃ | —N⟨tetrahydroisoquinoline⟩—COOCH(CH(CH₃)₂)—O—C(=O)—C₂H₅ (L) |

The $R_1$ protecting groups shown in Examples 39 and 41 to 43 and the $R_9$ protecting groups shown in Examples 24, 25, and 27 to 30 are removed as the last step in the synthesis. The $R_6$ ester groups shown in Examples 44 to 51 are not removed.

Similarly, the imino or amino acid esters of Col. I can be employed in the procedures of Examples 2 to 5 to obtain other compounds within the scope of this invention.

EXAMPLES 52–70

Following the procedure of Example 2 but employing the dicarboxylic acid mono ester shown below in Col. I one obtains the diester product shown in Col. II. Saponification yields the corresponding diacid which can then be converted to the disalt.

Col. I

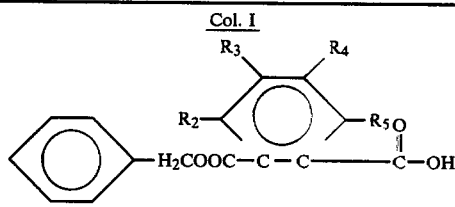

Col. II

-continued

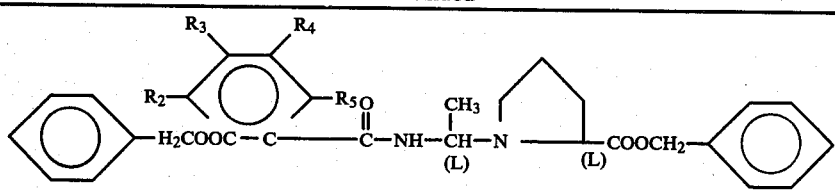

| Example | R₂ | R₃ | R₄ | R₅ |
|---|---|---|---|---|
| 52 | —CH₃ | —H | —H | —H |
| 53 | —H | —OCH₃ | —H | —H |
| 54 | —H | —SCH₃ | —H | —H |
| 55 | —CH₃ | —CH₃ | —CH₃ | —CH₃ |
| 56 | —H | —H | —OC₂H₅ | —H |
| 57 | —H | Br | —H | —H |
| 58 | —H | —H | —F | —H |
| 59 | —H | —CF₃ | —H | —H |
| 60 | —H | —H | —CH₂CCl₃ | —H |
| 61 | —H | —O—CH₂—⟨phenyl⟩ | —H | —H |
| 62 | —H | —H | —CH₂—O—CH₂—⟨phenyl⟩ | —H |
| 63 | —H | —⟨phenyl⟩ | —H | —H |
| 64 | —H | —H | —CH₂—⟨phenyl⟩ | —H |
| 65 | —H | —H | —⟨phenyl⟩—CH₃ | —H |
| 66 | —H | —CH₂—⟨phenyl⟩—F | —H | —H |
| 67 | —H | —H | —H | —NH—C(=O)—⟨phenyl⟩ |
| 68 | —⟨phenyl⟩ | —H | —H | —H |
| 69 | —H | —H | —H | —⟨phenyl⟩ |
| 70 | —Cl | —H | —H | —H |

The hydroxy protecting group shown in Examples 61 and 62 is removed as the last step in the synthesis.

Similarly, the imino or amino acid esters of Col. I of Examples 6 to 51 can be employed in the procedure os Examples 52 to 70 to obtain other compounds within the scope of the invention.

EXAMPLES 71–75

Following the procedure of Example 5 but employing the dicarboxylic acid mono ester shown below in Col. I one obtains the diester product shown in Col. II. Hydrogenation yields the corresponding diacid which can then be converted to the disalt.

Col. I

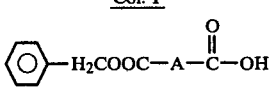

Col. II

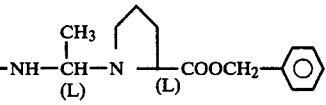

| Example | A |
|---|---|
| 71 | 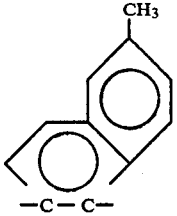 |
| 72 | 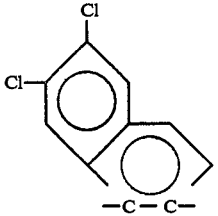 |
| 73 | 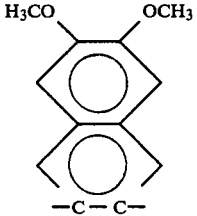 |
| 74 | 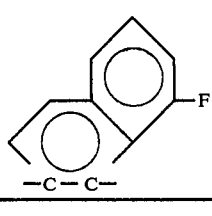 |
| 75 | (structure with F substituent) |

Similarly, the imino or amino acid esters of Col. I of Examples 6 to 51 can be employed in the procedure of Examples 71 to 75 to obtain other compounds within the scope of the invention.

EXAMPLE 76

1-[N-[[2-[[(2,2-Dimethyl-1-oxopropoxy)methoxy]-carbonyl]phenyl]carbonyl]-L-alanyl]-L-proline, lithium salt (a) Phthalic acid, mono[(2,2-dimethyl-1-oxopropoxy)-methyl]ester Phthalic acid is reacted with chloromethyl pivalate in the presence of diisopropylethylamine to yield phthalic acid, mono[(2,2-dimethyl-1-oxopropoxy)methyl]ester.

(b) 1-[N-[[2-[[(2,2-Dimethyl-1-oxopropoxy)methoxy]-carbonyl]phenyl]carbonyl]-L-alanyl]-L-proline, phenylmethyl ester The phthalic acid, mono[(2,2-dimethyl-1-oxopropoxy)methyl]ester from part (a) is reacted in an equimolar amount with L-alanyl-L-proline, phenylmethyl ester, p-toluenesulfonic acid salt in tetrahydrofuran in the presence of equimolar amounts of dicyclohexylcarbodiimide, 1-hydroxybenzotriazole hydrate, and diisopropylethylamine. The reaction mixture is worked up according to the procedure of Example 5(b) to give 1-[N-[[2-[[(2,2-dimethyl-1-oxopropoxy)methoxy]carbonyl]phenyl]carbonyl]-L-alanyl]-L-proline, phenylmethyl ester.

(c) 1-[N-[[2-[[(2,2-Dimethyl-1-oxopropoxy)methoxy]-carbonyl]phenyl]carbonyl]-L-alanyl]-L-proline, lithium salt The phenylmethyl ester product from part (b) is hydrogenated and the crude acid product is treated with lithium hydroxide and worked up according to the procedure of Example 5(c) to give 1-[N-[[2-[[(2,2-dimethyl-1-oxopropoxy)methoxy]carbonyl]phenyl]carbonyl]-L-alanyl]-L-proline, lithium salt.

EXAMPLES 77–81

Following the procedure of Example 76 but employing the alkylating agent shown in Col. I in place of the chloromethyl pivalate, one obtains the product listed in Col. II.

| Example | Col. I | Col. II |
|---|---|---|
| 77 | Br—CH₂—O—C(=O)—CH₃ | 1-[N—[[2-[[(acetyloxy)methoxy]-carbonyl]phenyl]carbonyl]-L-alanyl]-L-proline, lithium salt |
| 78 | Cl—CH(CH₃)—O—C(=O)—C₂H₅ | 1-[N—[[2-[[1-(ethylcarbonyloxy)-ethoxy]carbonyl]phenyl]carbonyl]-L-alanyl]-L-proline, lithium salt |
| 79 | Cl—CH₂—O—C(=O)—C₆H₅ | 1-[N—[[2-[[(benzoyloxy)methoxy]carbonyl]-phenyl]carbonyl]-L-alanyl]-L-proline, lithium salt |
| 80 | Cl—CH(CH(CH₃)₂)—O—C(=O)—C₂H₅ | 1-[N—[[2-[[2-methyl-1-(1-oxopropoxy)-propoxy]carbonyl]phenyl]carbonyl]-L-alanyl]-L-proline, lithium salt |
| 81 | Cl—CH(C₆H₁₁)—O—C(=O)—C₂H₅ | 1-[N—[[2-[[cyclohexyl(1-oxopropoxy)-methoxy]carbonyl]phenyl]carbonyl]-L-alanyl]-L-proline, lithium salt |

In a similar manner, esters of the products of Examples 2-75 can be prepared.

EXAMPLE 82

1-[N-[(2-Carboxyphenyl)carbonyl]-L-alanyl]-L-proline, disodium salt

1-[N-[(2-Carboxyphenyl)carbonyl]-L-alanyl]-L-proline (1 mmole) is dissolved in water (50 ml.). Aqueous sodium bicarbonate (0.1 N, 20 ml.) is added and the aqueous solution is lyophilized. It is then dissolved in water (10 ml.) and applied on a column of Sephadex chromatography gel G-10 and eluted with water. Fractions containing the desired product are pooled and lyophilized to give 1-[N-[(2-carboxyphenyl)carbonyl]-L-alanyl]-L-proline, disodium salt.

In a similar manner disodium or dipotassium salts of any of Examples 2 to 75 and sodium or potassium salts of Examples 76 to 81 can be prepared.

EXAMPLE 83

1000 tablets each containing the following ingredients:

| | |
|---|---|
| 1-[N—[(2-Carboxy-phenyl)carbonyl]-L-alanyl]-L-proline, disodium salt | 100 mg. |
| Corn starch | 50 mg. |
| Gelatin | 7.5 mg. |
| Avicel(microcrystalline cellulose) | 25 mg. |
| Magnesium stearate | 2.5 mg. | are prepared from sufficient bulk quantities by mixing the 1-[N-[(2-carboxyphenyl)carbonyl]-L-alanyl]-L-proline, disodium salt and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 1 to 81 can be prepared.

A similar procedure can be employed to form tablets containing 50 mg. of active ingredient.

EXAMPLE 84

Two piece #1 gelatin capsules each containing 50 mg. of 1-[N-(2-carboxy-4,5-dichlorobenzoyl)-L-alanyl]-L-proline, disodium salt are filled with a mixture of the following ingredients:

| | |
|---|---|
| 1-[N—(2-Carboxy-4,5-dichlorobenzoyl)-L-alanyl]-L-proline, disodium salt | 50 mg. |
| Magnesium stearate | 7 mg. |
| Lactose | 193 mg. |
| | 250 mg. |

In a similar manner capsules containing 50 mg. of the product of any of Examples 1 and 3 to 82 can be prepared.

EXAMPLE 85

An injectable solution is prepared as follows:

| | |
|---|---|
| 1-[N—[3-(Acetylamino)-2-carboxybenzoyl]-L-alanyl]-L-proline, disodium salt | 500 g. |
| Methyl paraben | 5 g. |
| Propyl paraben | 1 g. |
| Sodium chloride | 25 g. |
| Water for injection | 5 l. |

The active substance, preservatives, and sodium chloride are dissolved in 3 liters of water for injection and then the volume is brought up to 5 liters. The solution is filtered through a sterile filter and asceptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any of Examples 1 to 3 and 5 to 82.

EXAMPLE 86

1000 tablets each containing the following ingredients:

| | |
|---|---|
| 1-[N—[(2-Carboxy-phenyl)carbonyl]-L-alanyl]-L-proline, disodium salt | 100 mg. |
| Avicel | 100 mg. |
| Hydrochlorothiazide | 12.5 mg. |
| Lactose | 113 mg. |
| Cornstarch | 17.5 mg. |
| Stearic acid | 7 mg. |
| | 350 mg. | are prepared from sufficient bulk quantities by slugging the 1-[N-[(2-carboxyphenyl)carbonyl]-L-alanyl]-L-proline, disodium salt, Avicel and a portion of the stearic acid. The slugs are ground and passed through a #2 screen, then mixed with the hydrochlorothiazide, lactose, cornstarch, and remainder of the stearic acid. The mixture is compressed into 350 mg. capsule shaped tablets in a tablet press. The tablets are scored for dividing in half.

In a similar manner, tablets can be prepared containing 100 mg. of the product of any of Examples 2 to 81.

What is claimed is:

1. A compound of the formula $$R-\overset{O}{\underset{\|}{C}}-A-\overset{O}{\underset{\|}{C}}-NH-\overset{R_1}{\underset{|}{C}H}-\overset{O}{\underset{\|}{C}}-X$$

and a pharmaceutically acceptable salt thereof wherein

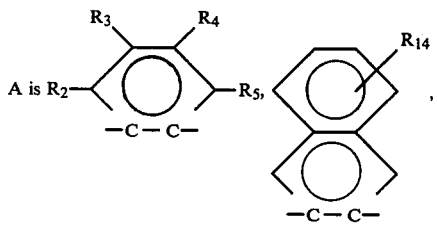

R is hydroxy, lower alkoxy, lower alkyl,

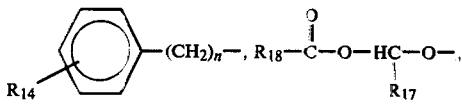

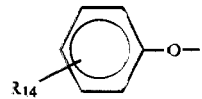

$R_1$ is hydrogen, lower alkyl, halo substituted lower alkyl,

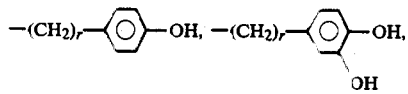

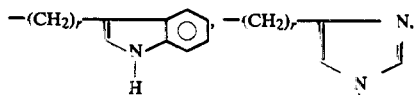

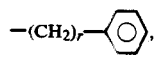

—(CH$_2$)$_r$—NH$_2$, —(CH$_2$)$_r$—SH, —(CH$_2$)$_r$—S—lower alkyl, —(CH$_2$)$_r$—S—lower alkyl,

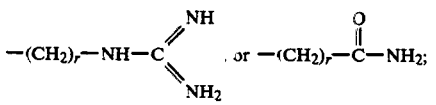

$R_2$, $R_3$, $R_4$ and $R_5$ are independently selected from the group consisting of hydrogen, lower alkyl of 1 to 4 carbons, lower alkoxy of 1 to 4 carbons, lower alkylthio of 1 to 4 carbons,

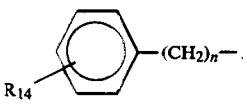

hydroxy, nitro, halo,
halo substituted lower alkyl of 1 to 4 carbons, hydroxy substituted lower alkyl of 1 to 4 carbons, lower

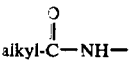

wherein said lower alkyl is of 1 to 4 carbons, and

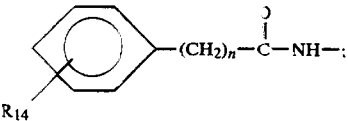

-continued

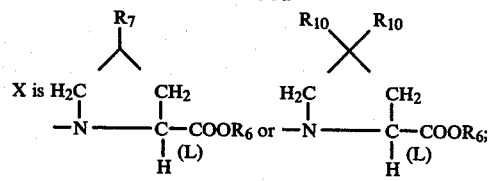

$R_7$ is hydrogen, lower alkyl, halogen, keto, hydroxy,

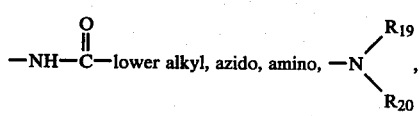

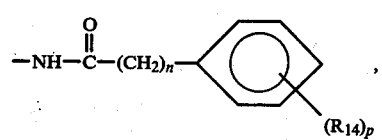

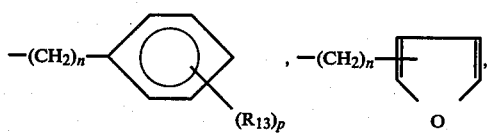

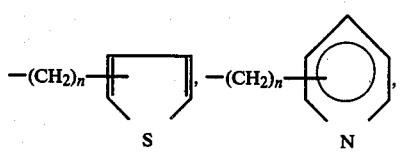

a 1- or 2-naphthyl of the formula

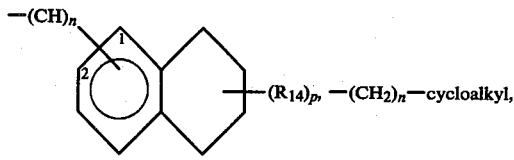

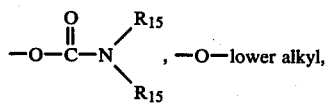

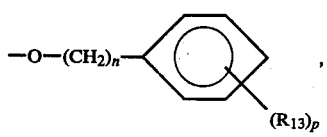

a 1- or 2-naphthyloxy of the formula

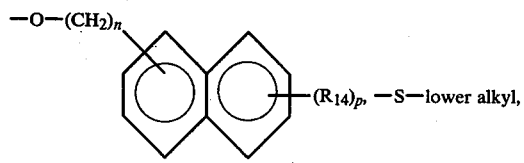

-continued

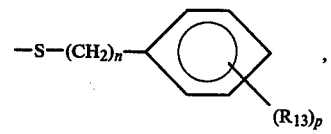

or a 1- or 2-naphthylthio of the formula

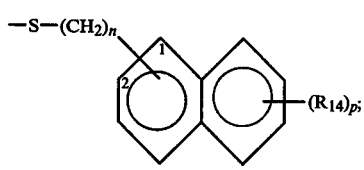

$R_{10}$ is halogen or $-Y-R_{16}$;

$R_{13}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl;

$R_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy;

n is zero, one, two, three, or four;

p is one, two or three provided that p is more than one only if $R_{13}$ or $R_{14}$ is hydrogen, methyl, methoxy, chloro, or fluoro;

$R_{15}$ is hydrogen or lower alkyl of 1 to 4 carbons;

Y is oxygen or sulfur;

$R_{16}$ is lower alkyl of 1 to 4 carbons,

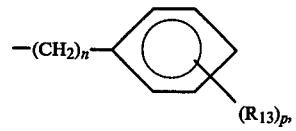

or the $R_{16}$ groups join to complete an unsubstituted 5- or 6-membered ring or said ring in which one or more of the carbons has a lower alkyl of 1 to 4 carbons or a di(lower alkyl of 1 to 4 carbons) substituent;

r is an integer from 1 to 4;

$R_{19}$ is lower alkyl, benzyl, or phenethyl;

$R_{20}$ is hydrogen, lower alkyl, benzyl or phenethyl;

$R_6$ is hydrogen, lower alkyl, benzyl, benzhydryl, salt forming ion, or

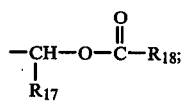

$R_{17}$ is hydrogen, lower alkyl, cycloalkyl of 3 to 7 carbons or phenyl;

$R_{18}$ is hydrogen, lower alkyl, lower alkoxy or phenyl; and

M is a salt forming ion.

2. A compound of claim 1 wherein

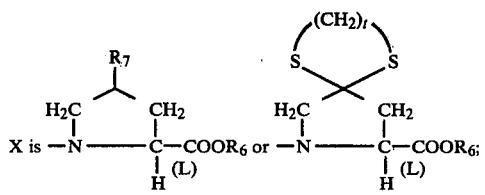

R₁ is hydrogen, straight or branched chain lower alkyl of 1 to 4 carbons,

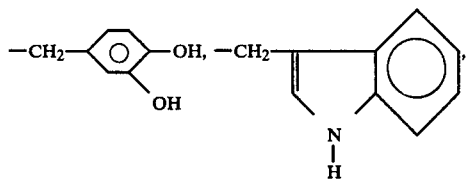

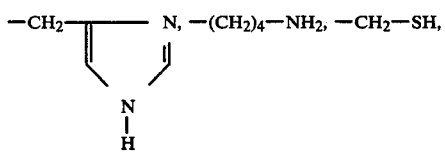

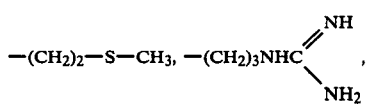

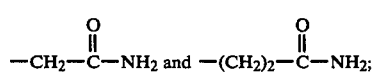

R₇ is hydrogen, cyclohexyl, lower alkoxy of 1 to 4 carbons,

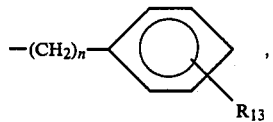

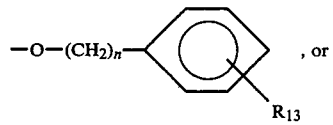, or

-continued

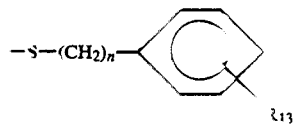

wherein n is zero, one or two and R₁₃ is hydrogen, methyl, methoxy, methylthio, Cl, Br, F or hydroxy;

t is two or three;

R₆ is hydrogen, an alkali metal salt ion, straight or branched chain alkyl of 1 to 4 carbons, or

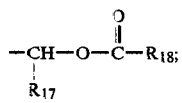

R₁₇ is hydrogen, straight or branched chain lower alkyl of 1 to 4 carbons, or cyclohexyl; and
R₁₈ is straight or branched chain lower alkyl of 1 to 4 carbons or phenyl.

3. A compound of claim 2 wherein

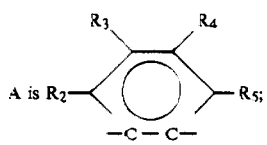

R₂, R₃, R₄ and R₅ are independently selected from the group consisting of hydrogen, methyl, methoxy, methylthio, phenyl, benzyl, nitro, halo, trifluoromethyl,

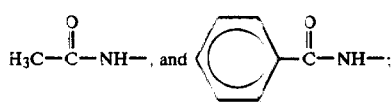

R is hydroxy, ethoxy, —OM or

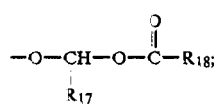

M is an alkali metal salt ion.

4. A compound of claim 3 having the formula

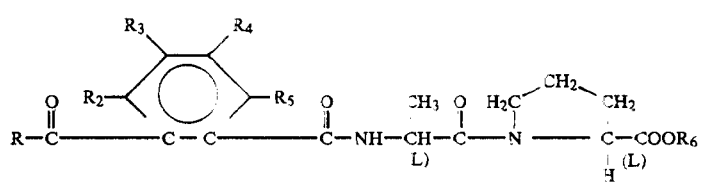

wherein
R₆ is hydrogen, ethyl,

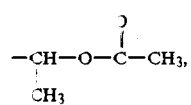

-continued

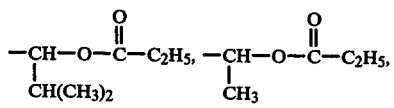

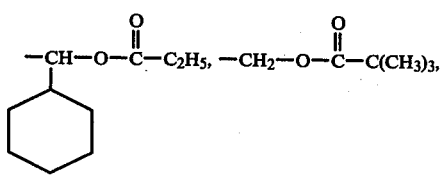

or an alkali metal salt ion; and

R is hydroxy or —OM wherein M is an alkali metal salt ion.

5. A compound of claim 4 wherein $R_2$, $R_3$, $R_4$, and $R_5$ are all hydrogen.

6. The compound of claim 5, 1-[N-[(2-carboxyphenyl)carbonyl]-L-alanyl]-L-proline.

7. A compound of claim 4 wherein
$R_2$ and $R_5$ are hydrogen; and
$R_3$ and $R_4$ are chloro.

8. The compound of claim 7, 1-[N-(2-carboxy-4,5-dichlorobenzoyl)-L-alanyl]-L-proline.

9. A compound of claim 4 wherein
$R_2$, $R_3$ and $R_4$ are hydrogen and $R_5$ is nitro.

10. The compound of claim 9, 1-[N-(2-carboxy-6-nitrobenzoyl)-L-alanyl]-L-proline.

11. A compound of claim 4 wherein $R_3$, $R_4$ and $R_5$ are hydrogen and $R_2$ is

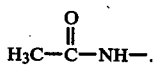

12. The compound of claim 11, 1-[N-[3-(acetylamino)-2-carboxybenzoyl]-L-alanyl]-L-proline.

13. A compound of claim 2 wherein

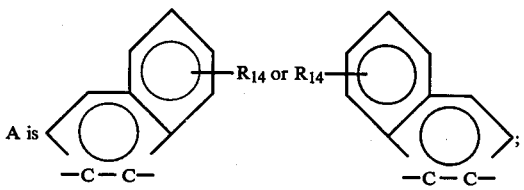

$R_{14}$ is hydrogen, methyl, methoxy, methylthio, chloro, bromo, fluoro, or hydroxy;
R is hydroxy, ethoxy, —OM, or

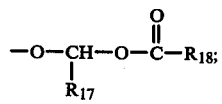

M is an alkali metal salt ion.

14. A compound of claim 13 having the formula

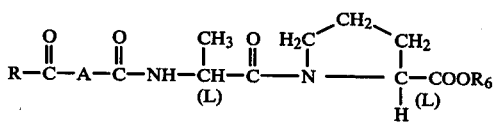

wherein
$R_6$ is hydrogen, ethyl,

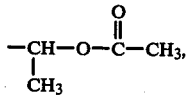

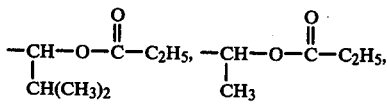

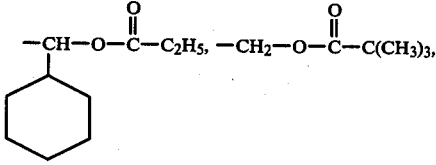

or an alkali metal salt ion; and

R is hydroxy or —OM wherein M is an alkali metal salt ion.

15. A compound of claim 14 wherein $R_{14}$ is hydrogen.

16. The compound of claim 15, 1-[N-[[2-carboxy-1-naphthalenyl]carbonyl]-L-alanyl]-L-proline, dilithium salt.

17. The compound of claim 15, 1-[N-[[1-carboxy-2-naphthalenyl]carbonyl]-L-alanyl]-L-proline, dilithium salt.

18. The method of treating hypertension in a mammalian specie which comprises administering an effective amount of a composition comprising a pharmaceutically acceptable carrier and hypotensively active compound of the formula

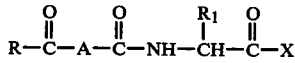

wherein R, $R_1$, A and X are as defined in claim 1.

* * * * *

UNITED STATES PATENT AND TRADEMARK OFFICE
CERTIFICATE OF CORRECTION

PATENT NO. : 4,456,595  
DATED : June 26, 1984  
INVENTOR(S) : Harold N. Weller III, et al.

It is certified that error appears in the above-identified patent and that said Letters Patent are hereby corrected as shown below:

In the title, delete "Aroly" and insert -- Aroyl --.  
Column 1, in the title, delete "Aroly" and insert -- Aroyl --.  
Column 2, line 35, after the formula should be inserted -- amino, HO-NH-, --.  
Column 2, line 61, delete "$-(CH_2)_r-NH_2-(CH_2)_r-SH$" and insert -- $-(CH_2)_r-NH_2, -(CH_2)_r-SH$ -- .  
Column 9, line 40, the top portion of the formula should read

--  --.

Column 20, Example 13, under X, the top portion of the formula should be --

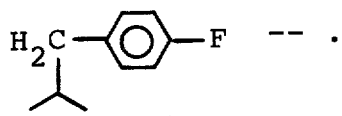 -- .

Column 20, Example 14, under X, the top portion of the formula should be --

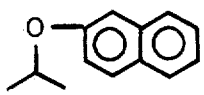

UNITED STATES PATENT AND TRADEMARK OFFICE
CERTIFICATE OF CORRECTION

PATENT NO. : 4,456,595
DATED : June 26, 1984
INVENTOR(S) : Harold N. Weller III, et al.

It is certified that error appears in the above-identified patent and that said Letters Patent are hereby corrected as shown below:

Column 30, Example 44, under X, the formula should be

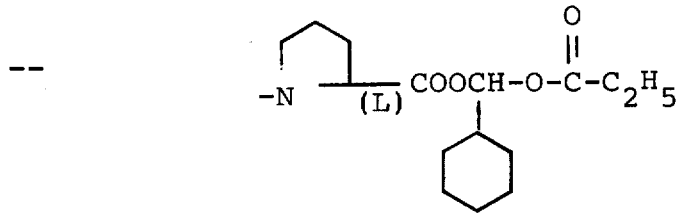

Column 40, line 10, after the formula should be inserted
-- amino, HO-NH-, lower alkoxy-HN-, or MO-;
Column 40, line 31, after $-(CH_2)_r-SH$, should be inserted
-- $-(CH_2)_r-OH$, --.

Signed and Sealed this

Fifth Day of November 1985

[SEAL]

Attest:

Attesting Officer

DONALD J. QUIGG

Commissioner of Patents and Trademarks